United States Patent [19]
Vernon et al.

[11] 3,991,755
[45] Nov. 16, 1976

[54] IONTOPHORESIS APPARATUS FOR APPLYING LOCAL ANESTHETICS

[75] Inventors: Jack A. Vernon; Murlan R. Kaufman, both of Portland; Robert E. Brummett, Milwaukie; Herman G. Bender, Portland, all of Oreg.

[73] Assignee: Medicon, Inc., Portland, Oreg.

[22] Filed: Jan. 2, 1975

[21] Appl. No.: 537,894

Related U.S. Application Data

[63] Continuation of Ser. No. 383,188, July 27, 1973, abandoned.

[52] U.S. Cl............................. 128/172.1; 128/409
[51] Int. Cl.² ........................................ A61N 1/30
[58] Field of Search ................ 128/172.1, 404–409, 128/416–418, 2.1 E, DIG. 4, 401, 419 R

[56] References Cited
UNITED STATES PATENTS

| | | | |
|---|---|---|---|
| 2,123,980 | 7/1938 | Warwick | 128/172.1 |
| 2,355,231 | 8/1944 | Moore | 128/172.1 |
| 2,949,107 | 8/1960 | Ziegler | 128/409 |
| 3,215,139 | 11/1965 | Dietz | 128/419 R |
| 3,476,670 | 11/1969 | Weiner | 128/2.1 E |
| 3,618,601 | 11/1971 | Richardson | 128/172.1 |
| 3,645,260 | 2/1972 | Cinotti et al. | 128/172.1 |
| 3,650,275 | 3/1972 | Mozel | 128/407 |
| 3,831,598 | 8/1974 | Tice | 128/172.1 |

FOREIGN PATENTS OR APPLICATIONS

| | | | |
|---|---|---|---|
| 712,703 | 7/1954 | United Kingdom | 128/409 |

OTHER PUBLICATIONS

Cumberbatch, "Iontophoresis with Therapeutic Ions", Essentials of Med. Elec., Kimpton, 1933, pp. 145–148.

Kovacs, "Galvanic Current-Therapeutic Uses", Electrotherapy and Light, pp. 124–127.

Dutton, "Phys. Therapy & Radiology," Clin. Med. & Surgery, Aug. 1935, vol. 42, No. 8, pp. 386–389.

Primary Examiner—Robert W. Michell
Assistant Examiner—Lee S. Cohen
Attorney, Agent, or Firm—Chernoff & Vilhauer

[57] ABSTRACT

Iontophoresis apparatus for applying local anesthetics to selected locations of animal bodies, particularly to the eardrum, comprises an electric circuit providing a source of direct current of constant and predetermined magnitude. Connected into the electric circuit are a first electrode adapted for placement in a quantity of ionized liquid anesthetic and a second electrode adapted for placement in contact with the body in a spaced location. A current adjustment circuit adjusts the current to selected values. Application of a constant current which may be progressively increased or diminished at the will of the operator provides effective iontophoretic action resulting in efficient anesthetization of the body area without adverse effects.

7 Claims, 11 Drawing Figures

IONTOPHORESIS APPARATUS FOR APPLYING LOCAL ANESTHETICS

This is a continuation of application Ser. No. 383,188, filed July 27, 1973, now abandoned.

BACKGROUND OF THE INVENTION

This invention relates to iontophoresis apparatus for applying local anesthetics to selected locations of animal bodies. The apparatus is useful particularly for applying local anesthetics in the external ear of humans and is described particularly with reference to such application. No limitation thereby is intended, however, since the apparatus with suitable modification may be used for the application of local anesthetics to any and all other body areas requiring local anesthetic and burdened by potentially acutely painful conditions, for example the area surrounding an ingrown toenail.

As is well known, the external auditory meatus (ear canal) includes a highly sensitive body area which is prone to infection and other physical failings requiring anesthesia before the indicated surgical or medical treatment may be performed. Serious attempts to anesthetize the ear began with the advent of cocaine in 1870. However, topical applications of this anesthetic have been disappointing from the standpoint of lack of effectiveness as well as from that of the production of adverse results. Similarly, dibucaine, tetracaine, cyclaine and phenol compounds all have been shown to be ineffective as local anesthetics for the purpose of anesthetizing the ear and in addition may cause undesirable side effects such as local tissue damage, allergic or toxic reactions, or contact dermatitis.

As a consequence, at the present time the procedure for obtaining anesthesia in the vast majority of ear surgeries is by local injection of anesthetic agents. This procedure is often as painful as the surgical pain it is designed to alleviate (e.g., the pain of a myringotomy, or piercing of the tympanic membrane). Consequently there is need for a painless procedure for anesthetizing sensitive areas such as the ear canal and drum. This need is particularly acute in the case of children.

It also is well known that iontophoresis when properly administered is an effective and painless method for driving anesthetic agents into the skin and thereby producing local anesthesia.

Iontophoresis is a process which utilizes direct electrical current to drive ionized chemical agents through the intact skin. For example, in aqueous media lidocaine hydrochloride disassociates into ions. The lidocaine ions responsible for its anesthetic action carry a positive electrical charge. Accordingly the anesthetizing lidocaine ions can be driven through the skin by the repelling action of the positive pole of a battery. Thus when iontophoresing lidocaine through the skin, the electrode contacting the lidocaine solution must be connected to the positive pole of the battery while the ground electrode which contacts the skin at some distant point is connected to the negative pole and provides a return path for the direct current.

The application of the techniques of iontophoresis to anesthetizing the auditory canal and ear drum was attempted as early as 1911. However, when considered from a practical standpoint, the results were unsatisfactory because the patients became vertiginous during and after treatment and some suffered permanent hearing losses. Also, the 1911 procedure was not free from pain and physical discomfort.

A further complicating circumstance is the fact that when the body is the medium for iontophoresis, fluctuations in current intensity often result which may produce pronounced symptoms of vertigo and pain, as well as unpleasant tingling sensations. Burns may be produced when the electrodes are improperly applied.

Fluctuations in current intensity are difficult to avoid when practicing iontophoresis. The intensity of the current passing through the body is a function of the electrical resistance of the body. This varies from patient to patient. In a given patient it also varies with such factors as nervous tension, fatigue, physical condition, emotions, sleep and mental state. This creates a problem, since if there is too little current, the anesthesia may be incomplete. if there is too much, there may be patient discomfort.

Accordingly it is the general purpose of the present invention to provide iontophoresis apparatus and method for applying local anesthetics to selected areas of the body, and especially to the ear drum and outer ear canal.

It is a particular object of the present invention to provide iontophoresis method and apparatus for local anesthesia the use of which is highly efficient in effectively anesthetizing selected body areas, without the accompaniment of undesirable side effects such as pain and vertigo or local tissue damage caused by burning or chemical action.

A further object of the present invention is the provision of iontophoresis apparatus for applying local anesthetics which apparatus is relatively simple and inexpensive in construction, reliable in operation, universally applicable with suitable modifications to anesthetizing various areas of the body, foolproof in its operation, and easily operated by personnel of average medical training readily available in any medical center.

Still other objects of the present invention are the provisions of iontophoretic anesthetizing apparatus which is sanitary in use; is reusable; will not shock the patient; permits the operator visually to inspect the site; does not damage the inner ear in any way; can be used with a wide variety of anesthetics; and is easily assembled and used.

DESCRIPTION OF THE DRAWINGS

The manner in which the foregoing and other objects of this invention are accomplished will be apparent from the accompanying specification and claims considered together with the drawings, wherein:

FIGS. 4 and 5 are detailed sectional views taken along lines 4—4 and 5—5 of FIG. 3 respectively.

FIG. 6 is a view in elevation of an electrode employed in conjunction with the herein described apparatus, illustrated in its use position in the ear canal.

FIG. 7 is a view similar to FIG. 6, but illustrating an alternate type of electrode.

FIG. 8 is a longitudinal section of the electrode of FIG. 6.

FIGS. 9 and 10 are bottom plan and fragmentary front elevations, respectively, of the electrode of FIG. 6 and FIG. 11 is a schematic circuit diagram illustrating an electric circuit including the herein described apparatus.

GENERAL STATEMENT OF THE INVENTION

Figure 1:
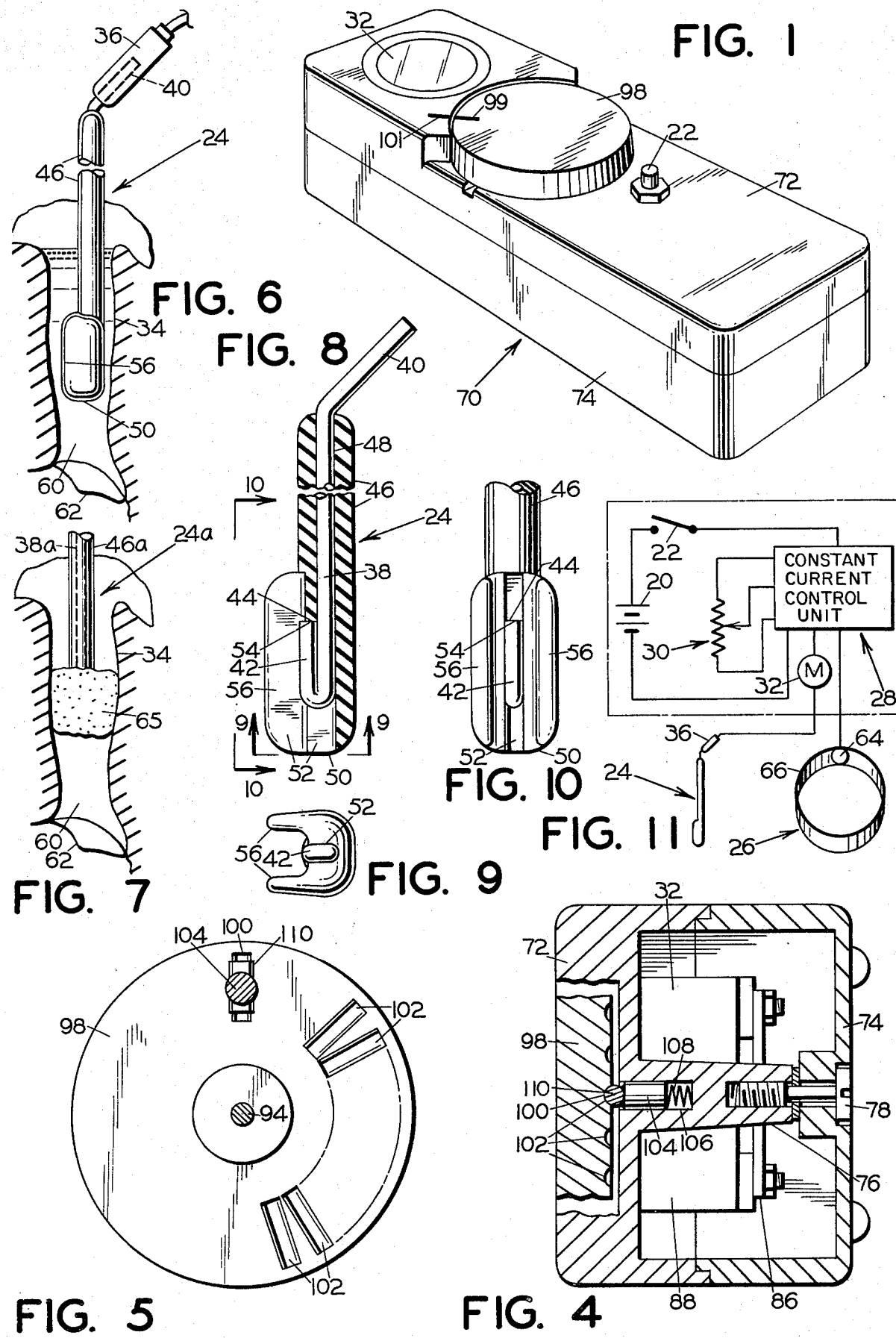
FIG. 1 is a top perspective view of the herein described iontophoresis apparatus for applying local anesthetics.

In its broad aspect, the iontophoresis apparatus of the pesent invention for applying local anesthetics to selected locations of animal bodies comprises an electric circuit providing a source of direct current of constant and predetermined magnitude which may be generated either manually or automatically. Connected in the circuit is a first electrode adapted for placement in a quantity of ionized liquid anesthetic contained in a selected body location, for example in the external ear canal.

Also connected in the electric circuit is a second electrode adapted for placement in contact with the body in a location spaced from the first electrode.

Current adjustment means is included in the circuit for adjusting the current to a predetermined constant value. Thus by applying to the ionized anesthetic a current which remains constant despite fluctuations in body resistant, and adjusting the magnitude of the current with time as anesthesia progresses, a highly effective anesthetization of the body area may be achieved without discomfort or adverse effect to the patient.

DETAILED DESCRIPTION OF A PREFERRED EMBODIMENT

Considering the foregoing in greater detail and with particular reference to the drawings:

The iontophoresis apparatus for applying local anesthetics of our invention is illustrated schematically in assembly in FIG. 11. The apparatus is powered by an electric circuit which includes batteries 20, on-off switch 22, the anesthetic-driving electrode 24, a ground electrode assembly 26, constant current control unit 28, current intensity adjustment unit 30 and ammeter 32. considering these in turn:

Batteries 20 are designed to provide a voltage and current of the desired strength. Illustrative of suitable batteries are the compact nine volt radio batteries which are generally available. Two such batteries suffice for the intended purpose.

In the form of the invention illustrated in FIGS. 6 and 8-11 inclusive, the anesthetic-driving electrode assumes a form suitable for insertion in the outer ear canal of a human, indicated at 34. The electrode is connected to the power source through a plug-in type connector 36 from which it may readily be detached for cleaning and sterilizing. Where the anesthesia-producing ion of the anesthetic is positively charged, electrode 24 is connected to the positive side of the electric circuit.

The electrode assembly comprises a length of electrically conducting wire of inert, non-toxic properties. Suitable for this use is inert stainless steel wire. Copper wire is unsuitable because of the possibility of introducing toxic copper salts into the system.

The electrode wire, indicated at 38 has an angularly bent shank end 40 and a reversely bent outer end 42. The latter end provides ample surface for electrical contact with the ionized anesthetic solution. It also provides an abutment surface 44.

Electrode wire 38 is housed in a sheath 46 of inert, sterilizable plastic material. A variety of plastics may be employed in the manufacture of the sheath, a suitable one being medical grade polypropylene.

The plastic sheath is provided with a longitudinal bore 48 dimensioned to receive wire 46 in sliding frictional engagement. Its outer end has an opening 50 which communicates with the exterior. Its lower portion also is provided with a longitudinal slot 52 which communicates with interior bore 48 and also with opening 50. The inner boundary of the slot is defined by an abutment 54 which registers with and abuts against abutment 44 on the end of reversely bent segment 42 of the electrode wire.

A pair of spaced tabs 56 is formed integrally with sheath 46. The tabs are mounted in the longitudinal direction, one on each side of slot 52. They serve a spacing and shielding function. Thus they space the exposed, reversely bent electrode wire segment 42 from the walls of the ear canal and shield the electrode from contact with the wall. This avoids the possibility of burning the patient in the use of the electrode.

It is to be noted further that tabs 56 space the electrode assembly from the walls of the ear canal so that the surgeon can see past the electrode and visually inspect the ear drum during the progress of anesthesia.

In the assembly of the electrode, the electrode wire with shank end 40 straight and outer end 42 reversely bent is inserted in and pushed through bore 48 of the sheath. It is advanced until abutment surface 44 of the wire abuts against abutment surface 54 of slot 52. Shank end 40 of the wire is bent angularly sufficiently to retain the electrode wire within the sheath. The assembly then is ready for insertion into the socket of plug type connector 36.

The anesthetic-driving electrode may assume different configurations to suit various purposes. The electrode above described is suitable for use in anesthetizing the tympanic membrane selectively. It accomplishes this for the reason that when the ear canal is filled with a quantity of ionized anesthetic solution 60 and the working end of the electrode immersed in the anesthetic solution, (as illustrated in FIG. 6,) the current passes through the tympanic membrane 62 almost exclusively because of the relatively low electrical resistance of the latter. It accordingly anesthetizes the membrane selectively.

Electrode 24 may assume different configurations where it is to be applied to the anesthesia of different body parts.

For example, if it is desired to anesthetize areas of the ear canal 34, the electrode form 24a illustrated in FIG. 7 may be employed. In this form of the invention the electrode wire 38a is housed in a plastic sheath 46a. Its exposed outer extremity is electrically connected to a wad of porous liquid absorbent material 54. This may comprise cotton batting, or filamentous synthetic fibers.

The dimensions of the wad are such that it is compressed slightly when it is inserted into the ear canal, thus assuring adequate surface contact with the side walls of the latter.

In use, the wad is soaked in liquid anesthetic and inserted in the ear canal. It contacts the walls of the latter to the exclusion of tympanic membrane 62. Accordingly, the lower electrical resistance of the latter is of no concern and the entire ear canal or any selected segment thereof may be anesthetized exclusively.

Other forms of anesthetic-driving electrode 24 also suggest themselves, depending upon the anatomical part to which they are to be applied. For example, the electrode may be cup-shaped or thimble-shaped if it is desired to place it over the end of a toe or finger to anesthetize the area surrounding an acutely sensitive ingrown toenail, or infected fingernail.

The companion ground electrode, indicated schematically at 26, comprises an electrode 64 of electrically conducting material. It preferably comprises an electrically conducting stainless steel plate having a contact area substantially greater than the exposed area of electrode wire 38.

Electrode plate 64 is adapted for placement on the surface of the body in an area electrically remote from the site to be anesthetized, for example on the ipsilateral upper arm.

It may be mounted on the upper arm by means of an arm band 66 fitted with burr type fasteners and suitably fastened to the electrode.

Electrode 64 is connected into the electric circuit by means of a snap-type fastener enabling its facile connection and disconnection. Such a connector is conventional and is not illustrated.

In order to prevent burning, it is important that electrode 64 be separated from the skin of the patient. This may be accomplished by applying conventional electrically conductive jelly or paste to the scrubbed skin area, applying a gauze pad to the jelly, applying a further quantity of electrode jelly to the exposed surface of the gauze pad and then superimposing the electrode, all in known manner.

Figure 2:
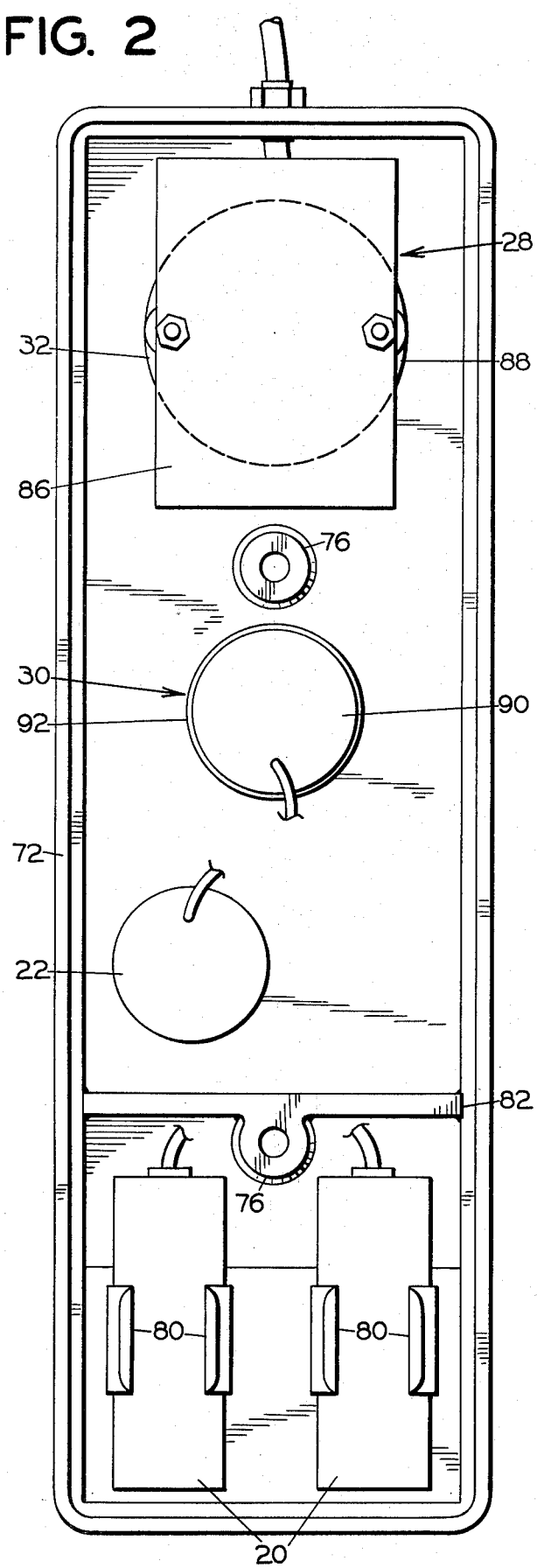
FIG. 2 is a bottom plan view of the apparatus with the cover removed.
Figure 3:
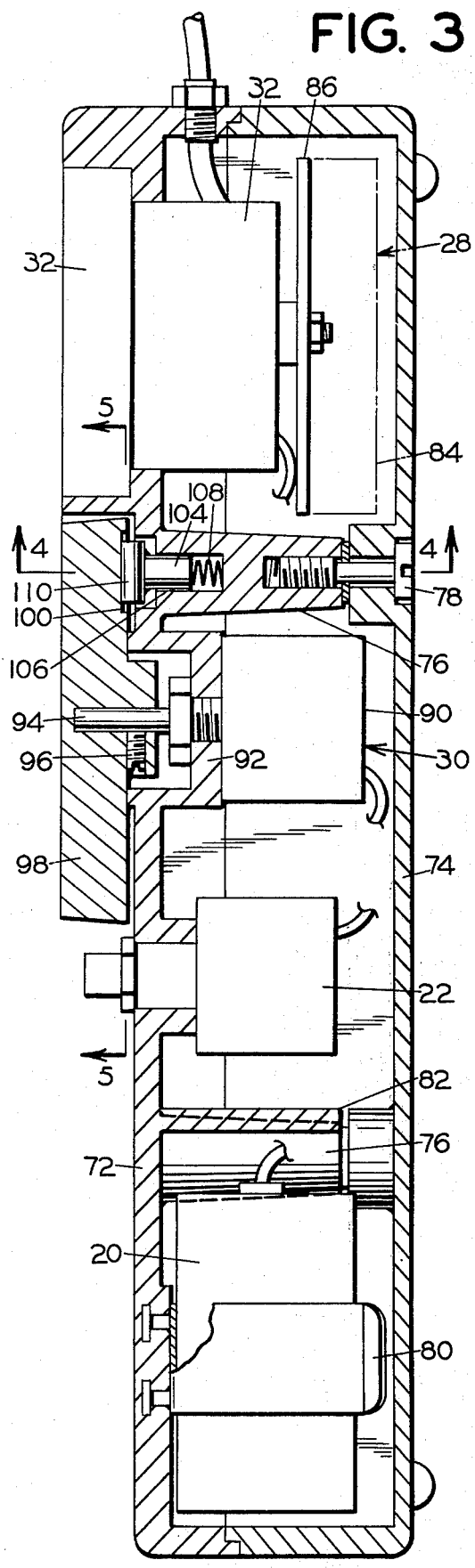
FIG. 3 is a longitudinal sectional view of the apparatus.

As noted above, it is important to the success of the presently described procedure that current of constant intensity be applied to the area to be anesthetized. Otherwise the patient may suffer unpleasant effects of vertigo and pain. Means 28 accordingly are provided for supplying a current of constant intensity to the electrodes. Means 30 further are provided for adjusting the current intensity to selected levels. Both of these means are contained in the instrument illustrated in detail in FIGS. 1–4 inclusive.

The instrument is housed in a longitudinally divided case 70 consisting of a top 72 and a bottom 74. Top 72 is formed with integral inwardly projecting posts 76 into which bolts 78 are threaded thereby enabling disassembleable assembly of the two parts.

Batteries 20 are releasably mounted in spring clips 80. They are separated by partition 82 from the rest of the assembly. As noted, they may comprise radio type nine volt batteries readily available in the market place.

The means provided for maintaining a constant current, indicated generally at 28, comprises preferably a conventional, commercially available printed circuit board of the class relying for its operation one zener diode and silicon transistor in conjunction with other components. The components, indicated schematically at 84, are mounted on a support plate 86 which in turn is bolted demountably to ammeter 32.

Associated with the printed circuit board is means indicated generally at 30 for adjusting the current strength to selected levels of intensity. The means employed for this purpose comprises a potentiometer 90 mounted on a bracket 92 and including a rotatably mounted potentiometer shaft 94.

Means are associated with shaft 94 for incrementally adjusting the current, which means are perceptible both tactually and audibly. The construction of the adjustment means is shown particularly in FIGS. 3 and 4.

Releasably secured to shaft 94 of the potentiometer by means of a set screw 96 is a control dial 98. Dial 98 has on its outer face a graduation mark 99 which registers with a companion graduation mark 101 in the off position of the instrument.

Detent means engage the underside of the dial to make possible adjustment of the dial in stages.

The detent means comprises a plurality of circumferentially spaced, radially extending detent grooves arranged in predetermined manner. For example one such groove 100 may be placed in the off position of the dial. A progressive sequence of on position grooves 102, FIG. 5, then may be arranged in a segmental area of the dial. There may be ten such grooves, corresponding to milliamp values of from 0.05 to 0.5.

Cooperating with detent grooves 100, 102 is a spring-pressed pawl comprising a shank 104 which is slidably received in a recess 106 in one of posts 76. A coil spring 108 is seated in the recess and bears against the undersurface of shank 104, biasing it in the outward direction. A cylindrical detent 110 is integrated to the outer end of shank 104, transversely thereof. It is dimensioned and arranged for reception in any of detent grooves 100, 102.

The entire instrument is compact so that it may be held in the hand. In its use, switch 22 is turned to the "on" position with detent 110 received in recess 100, this being the zero current delivery position. The operator then moves dial 98 counterclockwise, as viewed in FIG. 5. Thereupon the detent enters successively the various detent grooves 102. The entry is made positively into each groove. It is accompanied by an audible and tactual signal which easily is recognized by the operator. The value of the current supplied to the electrodes then may be read on ammeter 32.

In a typical local anesthetization of the human tympanic membrane by iontophoresis using the presently described apparatus and method, the patient lies on a table. His ear is examined through a Zeiss operating microscope.

The external auditory canal routinely is cleared of all debris and is filled with the anesthetic solution, which in a typical case may comprise 2% lidocaine and 1:2000 epinephrine. This requires between 1 and 1.5 cc.

The negative electrode 26 is placed on the ipsilateral arm and the positive electrode 24 is placed in the solution in the external auditory canal. The electrodes are prewired into the circuit.

The circuit is energized and then increased slowly by rotation of dial 98. The rate of current increase is such as to require about one minute to achieve a current value of one-half milliampere. The current is maintained at this level for ten minutes, after which it is reduced slowly over a period of 30 seconds. The slow change in current is needed to prevent a transient feeling of vertigo.

During the entire period of application of the electrode, the one-half milliampere current is kept constant by the battery-powered constant current power source 28. This delivers a continuous current even though changes in the resistance of the current path may occur. In turn, this prevents fluctuations of current flow that could induce dizziness, burning, or an unpleasant tingling sensation.

At the end of the iontophoresis period, the electrodes are removed. The patient turns his head to pour the anesthetic solution from the ear canal. The remaining solution is blotted out.

The anesthesia of the tympanic membrane is complete so that a myringotomy or other operation may be performed on the tympanic membrane. The anesthesia endures for from 1½ to 2 hours. It is accompanied by no adverse effects at the time of operation, nor are there adverse after effects. Pre and post iontophoresis audiograms reveal no hearing loss.

Having thus described our invention in preferred embodiments, we claim:

1. Iontophoresis apparatus for applying ionizable liquid local anesthetics to selected locations of animal bodies, the apparatus comprising:
   a. an electric circuit means providing a source of direct current of constant and predetermined magnitude;
   b. in the electric circuit means first electrode means adapted for placement in a quantity of ionizable liquid anesthetic contained in a selected body location to be anesthetized, said first electrode means comprising a length of electrically-conducting wire having inner and outer ends and an electrically-insulating sheath containing the wire, the sheath having inner and outer ends and being provided with a longitudinal slot at its outer end, the inner end of said wire being coupled to one pole of said current source and the outer end of said wire being exposed at said slot in said sheath, and said sheath further including a pair of laterally-extending tabs, one on each side of said slot and dimensioned for spacing the exposed outer end of said wire a predetermined distance from the body in the selected body location; and
   c. in the electric circuit means second electrode means connected to the other pole of the current source and adapted for placement in contact with the body in a location spaced from the first electrode means.

2. The apparatus of claim 1 wherein the slot in said sheath has an abutment surface, and the outer end of the electrically-conducting wire is reversely bent to provide an abutment surface in abutment with the abutment surface of the slot.

3. The apparatus of claim 1 wherein the first electrode means is dimensioned and arranged for insertion into the outer ear canal.

4. In iontophoresis apparatus for applying liquid anesthetics to the tympanic membrane and other portions of the ear canal, an electrode dimensioned for insertion into the ear canal and comprising:
   a. an electrically-conducting wire;
   b. means for coupling one end of the wire to a source of electric current;
   c. an electrically-insulating sheath substantially encasing the wire, said sheath having a cutaway section therein exposing a portion of said wire; and
   d. means cooperating with said sheath for spacedly positioning the exposed portion of said wire vertically with respect to the tympanic membrane and laterally with respect to the side walls of the ear canal and for shielding said exposed portion of the wire from direct contact with any portion of the ear canal.

5. The electrode of claim 4 wherein said last-named means (d) is integral to said sheath (c).

6. Iontophoresis apparatus for applying liquid anesthetics to the tympanic membrane, an electrode dimensioned for insertion in the ear canal and comprising:
   a. an electrically-conducting wire having inner and outer ends,
   b. means for connecting the inner end of the wire to a source of direct electric current,
   c. an electrically insulating sheath having inner and outer ends encasing the wire,
   d. the outer end of the sheath having a longitudinal slot exposing the outer end of the wire to contact with a liquid anesthetic contained in the ear canal, and a pair of spaced tabs positioned longitudinally, one on each side of the slot and parallel thereto for positioning the electrode laterally with respect to the side wall of the ear canal.

7. The electrode of claim 6 wherein the slot in said sheath is provided with an abutment surface and the outer end of the wire is reversely bent and provided with an abutment surface aligned with and in abutting relation to the abutment surface of the slot.

* * * * *